United States Patent
Cox et al.

(10) Patent No.: US 6,465,461 B1
(45) Date of Patent: *Oct. 15, 2002

(54) TRIAZINE COMPOUNDS FOR TREATMENT OF CNS DISORDERS

(75) Inventors: Brian Cox, Stevenage (GB); Mark Patrick Healy, Cambridge (GB); Malcolm Stuart Nobbs, Hitchin (GB); Gita Punjabhai Shah, Kenton (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/899,198

(22) Filed: Jul. 6, 2001

Related U.S. Application Data

(62) Division of application No. 09/582,058, filed as application No. PCT/EP98/08273 on Dec. 18, 1998, now Pat. No. 6,265,405.

(30) Foreign Application Priority Data

Dec. 22, 1997 (GB) .............................. 9726987

(51) Int. Cl.[7] .................... C07D 235/065; A61K 31/53; A61P 25/08; A61P 25/24
(52) U.S. Cl. ........................ 514/242; 544/182
(58) Field of Search .......................... 544/182; 514/242

(56) References Cited

U.S. PATENT DOCUMENTS

| | | | |
|---|---|---|---|
| 3,637,688 A | 1/1972 | Rees et al. | 260/249.9 |
| 5,658,905 A | 8/1997 | Critchley | 514/242 |
| 5,712,277 A | 1/1998 | Nakamura-Craig et al. | 514/242 |
| 5,801,171 A | 9/1998 | Nakamura-Craig et al. | 514/242 |
| 5,866,597 A | 2/1999 | Baxter | 514/242 |

FOREIGN PATENT DOCUMENTS

| | | |
|---|---|---|
| EP | 21120 | 8/1858 |
| EP | 24351 | 6/1859 |
| EP | 86502 | 2/1869 |
| EP | 142306 | 8/1873 |
| EP | 459829 | 9/1891 |
| EP | 459830 | 9/1891 |
| EP | 679645 | 7/1901 |
| EP | 0021121 A1 | 1/1981 |
| WO | WO 94/14780 | 7/1994 |
| WO | 96 20935 A | 7/1996 |
| WO | WO 97/20827 | 6/1997 |

OTHER PUBLICATIONS

Reduction of Sulfur Compounds, Chapter 10, pp 119–123 Reduction of Sulfur Compounds (Except Sulfur Derivatives of Aldehydes, Ketones, and Acids), "Reductions in Organic Chemistry," Second Edition, Milos Hudlicky, ACS Monograph 188, 1996, American Chemical Society, Washington, D.C.

Chemical Abstracts, vol. 118, No. 13, Mar. 1993 Columbus Ohio, US; abstract No. 116561 Cheung et al "An in vitro investigation of the action of Imotrigine on neuronal voltage–activated sodium channels" and Epilepsy Res. (1992), 13(2)m 197–12I USSBL 0920–1211.

Calabrese et al Am J Psychiatry 156:7, Jul. 1999 1019–1023 Spectrum of Activity of Lamotrigine in Treatment–Refractory Bipolar Disorder *copy attached.

*Primary Examiner*—Mukund J. Shah
*Assistant Examiner*—Venkataraman Balasubramanian
(74) *Attorney, Agent, or Firm*—Nixon & Vanderhye P.C.

(57) ABSTRACT

A compound of formula (I)

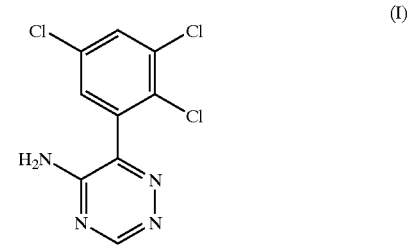

and pharmaceutically acceptable prodrugs, salts and solvates thereof.

3 Claims, No Drawings

TRIAZINE COMPOUNDS FOR TREATMENT OF CNS DISORDERS

This application is a division of application Ser. No. 09/582,058, filed Jul. 12, 2000, the entire content of which is hereby incorporated by reference in this application which is a 371 of PCT/EP98/08273 filed on Dec. 12, 1998.

The present invention relates to a triazine compound which is useful in the treatment of central nervous system (CNS) diseases and disorders and to its pharmaceutically acceptable derivatives, to pharmaceutical compositions containing them, to their use in the treatment of such disorders and to methods of preparation.

EP-A-0021121 and EP-A-0247892 describe 3,5-diamino triazines, for example 3,5diamino-6-(2,3dichlorophenyl)-1,2,4-triazine (lamotrigine), which are active in the treatment of disorders of the CNS and are particularly useful in the treatment of epilepsy.

The present invention relates to a 5-amino triazine derivative which is a sodium channel blocker. This compound is a surprisingly potent anti-convulsant having increased potency with respect to lamotrigine and increased selectivity in terms of CNS side-effects and inhibition of the enzyme dihydrofolate reductase. The compound is therefore useful in the treatment of CNS diseases such as epilepsy.

Accordingly, the invention provides a compound of formula (I)

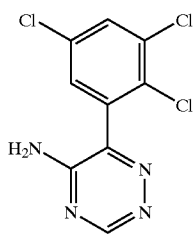

(I)

i.e. 5-amino-6-[2,3,5-trichlorophenyl]-1,2,4-triazine and pharmaceutically acceptable derivatives thereof.

By pharmaceutically acceptable derivative is meant any pharmaceutically acceptable salt or solvate of the compounds of formula (1), or any other compound which upon administration to the recipient is capable of providing (directly or indirectly) a compound of formula (I) or an active metabolite or residue thereof (eg. a prodrug). Reference hereinafter to the compounds of formula (I) includes the compound of formula (I) and pharmaceutically acceptable derivatives thereof.

Suitable pharmaceutically acceptable salts of the compound of formula (I) include acid addition salts formed with inorganic or organic acids, preferably inorganic acids, e.g. hydrochlorides, hydrobromides and sulphates.

Suitable prodrugs are well-known in the art and include N-acyl derivatives, for example at either of the four nitrogens in the compounds of formula (I), for example simple acyl derivatives such as acetyl, propionyl and the like or groups such as R—O—CH$_2$-nitrogen or R—O—C(O)-nitrogen.

The compounds of formula (I) are particularly useful as anticonvulsants. They are therefore useful in treating epilepsy. They may be used to improve the condition of a host, typically a human being, suffering from epilepsy. They may be employed to alleviate the symptoms of epilepsy in a host "Epilepsy" is intended to include the following seizures: simple partial seizures, complex partial seizures, secondary generalised seizures, generalised seizures including absence seizures, myoclonic seizures, clonic seizures, tonic seizures, tonic clonic seizures and atonic seizures.

The compounds of formula (I) are additionally useful in the treatment of bipolar disorder, alternatively known as manic depression. Type I or II bipolar disorder may be treated. The compounds of formula (I) may thus be used to improve the condition of a human patient suffering from bipolar disorder. They may be used to alleviate the symptoms of bipolar disorder in a host. The compounds of formula (I) may also be used in the treatment of unipolar depression.

The compounds of formula (I) are useful as analgesics. They are therefore useful in treating or preventing pain. They may be used to improve the condition of a host, typically a human being, suffering from pain. They may be employed to alleviate pain in a host. Thus, the compounds of formula (I) may be used as a preemptive analgesic to treat acute pain such as musculoskeletal pain, post operative pain and surgical pain, chronic pain such as chronic inflammatory pain (eg. rheumatoid arthritis and osteoarthritis), neuropathic pain (e.g. post herpetic neuralgia, trigeminal neuralgia and sympathetically maintained pain) and pain associated with cancer and fibromyalgia. The compounds of formula (I) may also be used in the treatment or prevention of pain associated with migraine.

The compounds of formula (I) are further useful in the treatment of functional bowel disorders which include non-ulcer dyspepsia, non cardiac chest pain and in particular irritable bowel syndrome. Irritable bowel syndrome is a gastrointestinal disorder characterised by the presence of abdominal pain and altered bowel habits without any evidence of organic disease. The compounds of formula (I) may thus be used to alleviate pain associated with irritable bowel syndrome The condition of a human patient suffering from irritable bowel syndrome may thus be improved.

The compounds of formula (I) may also be useful in the treatment of neurodegenerative diseases, such as Alzheimer's disease, ALS, motor neuron disease, Parkinson's disease, muscular sclerosis, macular degeneration and glaucoma. The compounds of formula (I) may also be useful in neuroprotection and in the treatment of neurodegeneration following stroke, cardiac arrest, pulmonary bypass, traumatic brain injury, spinal cord injury or the like.

The compounds of formula (I) are further useful in the treatment of tinnitus.

Still further, the compounds of formula (I) are also useful in preventing or reducing dependence on, or preventing or reducing tolerance or reverse tolerance to, a dependence inducing agent. Examples of dependence inducing agents include opioids (eg morphine), CNS depressants (eg ethanol), psychostimulants (eg cocaine) and nicotine.

There is therefore further provided by the present invention, use of a compound of formula (I) or a pharmaceutically acceptable derivative thereof for use in human and veterinary medicine.

There is therefore further provided by the present invention, use of a compound of formula (I) in the manufacture of a medicament for use in the treatment of a disorder substantially as hereinbefore described.

The present invention further comprises a method of treating a patient suffering from, or susceptible to, a disorder substantially as hereinbefore described, which method comprises administering to the patient a therapeutically effective amount of a compound of formula (I).

The term "treatment" as used herein includes the treatment of established disorders, and also includes the prophylaxis thereof The precise amount of the compounds of formula (I) administered to a host, particularly a human patient, will be the responsibility of the attendant physician However, the dose employed will depend upon a number of factors including the age and sex of the patient, the precise condition being treated and its severity, and the route of administration.

The compound of formula (I) may be administered at a dose of from 0.1 to 10 mg/kg body weight per day and more particularly 0.3 to 3 mg/kg body weight per day, calculated as the free base. The dose range for adult human beings is generally from 8 to 1000 mg/day, such as from 35 to 800 mg/day, preferably 10 to 200 mg/day or 20 to 200 mg/day, calculated as the free base.

The compounds of formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

While it is possible for the compounds of formula (I) to be administered as the raw chemical, it is preferable to present it as a pharmaceutical formulation. The formulations of the present invention comprise the compounds of formula (I) thereof together with one or more acceptable carriers or diluents therefor and optionally other therapeutic ingredients. The carrier(s) must be "acceptable" in the sense of being compatible with the other ingredients of the formulation and not deleterious to the recipient thereof.

The formulations include those suitable for oral, parenteral (including subcutaneous e.g by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compound of formula (I) or a pharmaceutically acceptable acid addition salt thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

Preferred unit dosage formulations are those containing an effective daily dose, as herein above recited, or an appropriate fraction thereof, of the active ingredient. Conveniently that may be from 5 mg to 1000 mg, such as from 8 mg to 1000 mg, more conveniently 35 mg to 800 mg, and most conveniently 10 to 200 mg or 20 to 200 mg, calculated as the free base.

The compounds of formula (I) may be used in combination with other therapeutic agents, for example other anticonvulsants. When compounds of formula (I) are used in combination with other therapeutic agents, the compounds may be administered either sequentially or simultaneously by any convenient route. The invention thus provides, in a further aspect, a combination comprising a compound of formula (I) or a pharmaceutically acceptable derivative thereof with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease, the dose of each compound may differ from that when the compound is used alone. Appropriate doses will be readily appreciated by those skilled in the art.

The present invention provides a process for preparing compounds of formula (I) and pharmaceutically acceptable derivatives thereof.

The compounds of formula (I) may be prepared by the methods outlined below which form a further aspect of the invention.

According to a general process (A), which forms a further aspect of the invention, a compound of formula (I) may be prepared under suitable reaction conditions from a compound of formula (II)

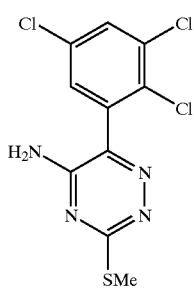

(II)

for example, by reduction, preferably using a reduction metal, such as Raney nickel, and a source of hydrogen, such as hydrazine monohydrate, in a suitable solvent, such as ethanol, preferably at elevated temperature, for example between 70–750° C.

According to another process (B), which forms a further aspect of the invention, a compound of formula (I) may be prepared under suitable reaction conditions by reacting a compound of formula (III)

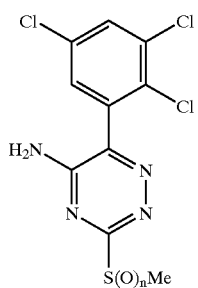

(III)

wherein n may be one or two, with a reducing agent. Suitable reducing agsents include borohydrides, preferably sodium borohydride. The reaction may be carried out in a solvent mixture, such as an ether, preferably tetrahydrofuran and an alcohol, preferably t-butanol and at room temperature.

A compound of formula (III) may be prepared under suitable reaction conditions by reacting a compound of formula (II) with an oxidising agent, such as a peracid, for example potassium peroxymonosulfate or m-chloroperbenzoic acid and at a reduced temperature, for example, <5° C. and this forms a further aspect of the invention.

A compound of formula (II) may suitably be prepared by reacting 2,3,5-trichlorobenzoyl cyanide with a S-methylthiosemicarbazide salt, preferably hydroiodide, in the presence of a dilute mineral acid, preferably dilute sulphuric acid and this forms a further aspect of the invention.

A compound of formula (II) may alternatively be prepared under suitable reaction conditions by the photolysis of a solution of a compound of formula (IV), at between 320 and 750 nm

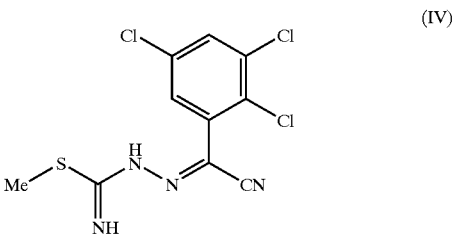

(IV)

in a suitable solvent, such as an alcohol, preferably propan-1-ol and at elevated temperature, for example the reflux temperature of the solvent and this forms a further aspect of the invention.

2,3,5-trichlorobenzoyl cyanide and S-methylthiosemicarbazide may be prepared according to conventional procedures and this forms a further aspect of the invention.

A compound of formula (IV) may be prepared under suitable reaction conditions by reacting a compound of formula (V)

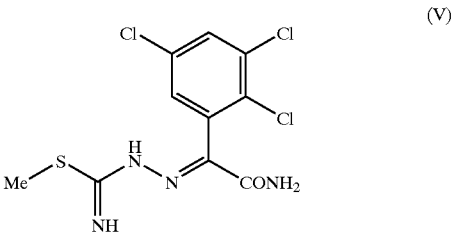

(V)

with a dehydrating agent, preferably diphosphoryl chloride and this forms a further aspect of the invention.

A compound of formula (V) may suitably be prepared by the reaction of a compound of formula (VI)

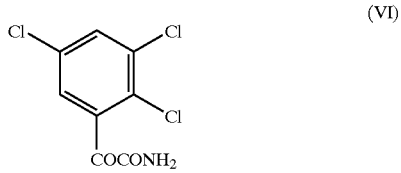

(VI)

with a S-methylthiosemicarbazide salt, preferably hydroiodide, in a suitable solvent, for example ethanol, and at elevated temperature, for example 50° C. and this forms a further aspect of the invention.

A compound of formula (VI) may be prepared under suitable reaction conditions by reacting 2,3,5-trichlorobenzoyl cyanide with a strong aqueous acid, preferably concentrated hydrochloric acid, which forms a further aspect of the invention.

Prodrugs of the compounds of formula (I) may be prepared according to conventional procedures.

The following Examples which should not be construed as constituting a limitation thereto are provided to illustrate the invention.

Intermediate 1

2,3,5-Trichlorobenzoic Acid 2,3,5-Trichlorobenzaldehyde (197.40 g, 0.94 mole, Lancaster) was dissolved in t-butanol (785 ml), stirred and heated under nitrogen at 50° C. 2M Aqueous sodium hydroxide (940 ml) was warmed to 50° C. and added to the solution of the aldehyde. Hydrogen peroxide (27.50% aqueous, 699 g, 5.65 mole) was added using a dosing pump over 45 min, maintaining the temperature between 57–60° C. The reaction mixture was then stirred and heated under nitrogen for a further hour, cooled and evaporated in vacuo. The residual slurry was filtered and the filtrate was washed with toluene (2×300 ml) and then acidified (pH1) with 5M hydrochloric acid whilst stirring vigorously. The resulting thick white precipitate was filtered, washed with water (3×300 ml) and dried in vacuo at 50° C. Yield 180 g (85%). M.p. 155–158° C. (froth).

Intermediate 2

2,3,5-Trichlorobenzoyl Chloride 2,3,5-Trichlorobenzoic acid (75 g, 0.33 mole, Example 1) and thionyl chloride (197.47 ml, 271.32 g, 2.28 mole) were refluxed in anhydrous toluene (350 ml) at 120° C. for 3 hrs. The reaction mixture was cooled to room-temperature and evaporated in vacuo. The residue was azeotroped with anhydrous toluene (3×100 ml) to give a brown viscous oil.

An alternative preparation can be carried out as follows:

2,3,5-Trichlorobenzoic acid (75 g, 333 mmol, 1 eq) was added to toluene (225 ml) and the slurry was heated at reflux for 2 hours with a dean-stark apparatus attached. The acid dissolved into the solution upon heating. The solution was cooled with good stirring, and pyridine (0.2 ml, cat.~0.5 mol %) and thionyl chloride (26.7 ml, 365 mmol, 1.1 eq) were added via a dropping funnel over a period of 1 hour, maintaining an internal temperature between 70–80° C. Once the addition was complete, the mixture was heated at reflux for 2 hours. The solution was cooled, the volatiles were removed in vacuo, and then azeotroped with toluene (2×50 ml) to give a clear yellow oil as the product.

Intermediate 3

2,3,5-Trichlorobenzoyl Cyanide

Copper (I) cyanide (63.88 g, 0.71 mole), potassium iodide (108.20 g, 0.65 mole) were refluxed in anhydrous xylene (590 ml) at 150° C. for 24 hrs using Dean-Stark apparatus. A solution of 2,3,5-trichlorobenzoyl chloride in anhydrous xylene (150 ml) was added and the resulting suspension was refluxed under nitrogen at 150° C. for 3 days. The suspension was filtered and the filtrate was evaporated in vacuo. δ(CDCl$_3$): 7.80 (s, 1H), 8.0 (s, 1H).

An alternative preparation can be carried out as follows:

Potassium iodide (66.25 g, 400 mmol, 1.2 eq) (sieved to particle size <1 mm) and copper (I) cyanide (36 g, 400 mmol, 1.2 eq), in xylene (400 ml) were heated at reflux for 3 hours with a dean-stark apparatus attached. The mixture was cooled, and 2,3,5-trichlorobenzoyl chloride, in xylene (100 ml), was added. The mixture was heated at reflux with a dean-stark apparatus attached. The mixture gradually turned red/orange over 30 minutes, and a light brown solution was obtained overnight.

The mixture was heated at reflux for 40 hours, then cooled, and the inorganics filtered off. The xylene was removed in vacuo a @ 55° C., azeotroped with toluene (2×50 ml), then petroleum ether 60–80 (260 ml) was added via a buchi inlet, to give a brown solution. On cooling, a brown precipitate was formed. The solution was stirred at room temperature overnight, the solid filtered off, and washed with petroleum ether 60–80 (100 ml). The solid was sucked dry under nitrogen blanket to afford a first crop of yellow solid, 2,3,5-trichlorobenzoyl nitrile (45.5 g, 58.1%).

The filtrate was concentrated, left to stand for 24 hours, and a second crop was then collected (6.8 g, 8.7%), followed by a third crop (5.3 g, 6.8%). Total yield (57.6 g, 73.8%). N.m.r.(d$_6$-DMSO) dppm: 8.03(d,1H), 8.34(d, 1H).

Intermediate 4

S-Methylthiosemicarbazide Hydroiodide

Thiosemicarbazide (448 g, 0.50 mole, Aldrich) and iodomethane (300 ml, 5 mole) were refluxed in 95% ethanol (2000 ml ) for 5 hrs and then cooled to room-temperature. The desired product was filtered, washed with ether (3×300 ml) and dried in vacuo. Yield 647 g. M.p. 138–140° C.

Intermediate 5

3-Thiomethyl-5-amino-6-[2,3,5-trichlorophenyl]-1,2,4-triazine [Formula (II)]

Route A

S-Methylthiosemicarbazide hydroiodide (38.59 g, 0.17 mole) was suspended in dilute sulphuric acid (95.83 ml concentrated sulphuric acid/95.83 ml water) and stirred at room-temperature for one hour. A solution of 2,3,5-trichlorobenzoyl cyanide (18 g, 0.077 mole) in acetonitrile (90 ml) was slowly added and the resulting mixture was stirred at room-temperature for eleven days. The reaction mixture was diluted with water and extracted with ethylacetate (3×250 ml) The ethylacetate layer was washed with water (2×300 ml), dried over anhydrous magnesium sulphate, filtered and evaporated the filtrate in vacuo The residue was dissolved in propan-1-ol (500 ml) and refluxed at 130° C. for 4 hrs. The reaction mixture was cooled to room-temperature and evaporated in vacuo. The residue was partitioned between 2N aqueous sodium hydroxide(100 ml) and ethylacetate (300 ml). The ethylacetate layer was washed with water (2×100 ml), dried over anhydrous magnesium sulphate, filtered and evaporated the filtrate in vacuo. The residue was purified by 'flash chromatography' using cyclohexane to 1:3 cyclohexane:ether as the eluent. Yield 1.90 g (8%) M.p. 138–140° C.

Route B

2-[S-Methylthiosemicarbazono]-2-[2,3,5-trichlorophenyl]-acetonitrile (1.00 g, 3.11 mmol) was stirred in propan-1-ol (40 ml) and heated to reflux under nitrogen. A 300 Watt tungsten lamp was shone onto the mixture and the reaction left under these conditions for forty-eight hours. The reaction was cooled to room temperature, then the lamp was switched off and the solution evaporated in vacuo to leave a dark oil which crystallised on standing. The solid was triturated with methanol, filtered and dried to give product, 3-thiomethyl-5-amino-6-[2,3,5-trichlorophenyl]-1,2,4-triazine. Yield 770 mg (77.0%). N.M.R. (d$_6$-DMSO) δ ppm: 2.50(s, 3H), 7.15(broad s, 1H), 7.63(d, 1H), 7.90(broad s, 1H), 8.00(d, 1H). LC/MS, Electrospray positive (M+1)$^+$= 321/323.

Intermediate 6

3-Methylsulfoxy-5amino-6-[2,3,5-trichlorophenyl]-1,2,4-triazine [Formula (III)]

3-Thiomethyl-5-amino-6-[2,3,5-trichlorophenyl]-1,2,4-triazine (6 g, 18.7 mmol, 1 eq), was suspended in dichloromethane (650 ml), and cooled to 5° C.

m-Chloroperbenzoic acid (5.669, 18.7 mmol, assumed 57%, ~1 eq) was added in one portion and stirred at <10° C. for 20 minutes, under nitrogen, resulting in a clear yellow solution. Analysis by TLC (1:1 cyclohexane ethyl acetate) showed no remaining starting material. The reaction was quenched by the addition of sodium sulfite (10 g) and water (200 ml) to the vigourous stirred solution. The layers were separated and the organic layer was washed with 10% aqueous sodium sulfite solution (100 ml). Merck peroxide test strips were found to be negative. The organic layer was washed with saturated sodium hydrogen carbonate (200 ml), then washed with a brine solution (200 ml), and then dried over anhydrous magnesium sulfate. The organic solution was filtered and the solvent was removed in vacuo to afford a yellow solid, 3-Methylsulfoxy-5-amino-6-[2,3,5-trichlorophenyl]-1,2,4-triazine. Yield 5.82 g (92.2%).

N.m.r.(CDCl$_3$) δ ppm: 3.05(s,3H), 7.39(d,1H), 7.69(d, 1H). LC/MS Electrospray positive (M+1)$^+$=337/339.

Intermediate 7

2-Oxo-2-[2,3,5-trichlorophenyl]-acetamide [Formula (VI)]

2,3,5-Trichlorobenzoyl cyanide (10.0 g, 46 mmole) was added to concentrated hydrochloric acid (140 ml) and stirred at room temperature for forty-eight hours. The suspension was diluted with water (100 ml) and then filtered. The light-brown solid was washed with water, then air-dried for one hour. The crude product was then dissolved in ethyl acetate (400 ml), washed with saturated aqueous sodium hydrogen carbonate solution (2×300 ml), followed by brine (300 ml) and then dried over magnesium sulphate, filtered and evaporated to leave a beige solid. This solid was triturated in hexaneltoluene (200 ml), filtered and dried in vacuo, to yield an off-white solid, 2-oxo-2-[2,3,5-trichlorophenyl]-acetamide. Yield 7.02 g (65.3%). N.M.R. (d$_6$-DMSO) δ ppm: 7.77(d, 1H), 8.09(d, 1H), 8.13(broad s, 1H), 8.48(broad s, 1H). LC/MS, Electrospray negative (M−1)$^-$=250/252.

Intermediate 8

2-[S-Methylthiosemicarbazono]-2-[2,3,5-trichlorophenyl]-acetamide [Formula (V)]

2-Oxo-2-[2,3,5-trichlorophenyl]-acetamide (5.00 g, 19.8 mmol) and S-methylthiosemicarbazide hydroiodide (9.20 g, 39.5 mmol) were suspended in ethanol (100 ml) and heated at 50° C., under nitrogen, overnight. As thin layer chromatography showed the starting material was still present, a further quantity of S-methylthiosemicarbazide hydroiodide (4.00 g, 17.2 mmol) was added and stirring was continued at 50° C. for two hours. The reaction mixture was evaporated in vacuo to yield a brown oil. This oil was dissolved in ethyl acetate (400 ml), washed with water (300 ml), then brine (300 ml), dried over magnesium sulphate, filtered and evaporated in vacuo to afford a yellow-brown gum. This gum was purified by column chromatography using 1:1 ethyl acetate:hexane as the eluent. The product, predominantly the E isomer, was obtained as a pale yellow solid, yield 4.25 g (63.2%). N.M.R. (d$_6$-DMSO) δ ppm: 2.14(s, 3H), 7.28(d,1H), 7.31(broad s,1H), 7.84(d,1H), 8.28(broad s,1H). LC/MS, Electrospray positive (M+1)$^+$=339/341.

Intermediate 9

2-[S-Methylthiosemicarbazono]-2-[2,3,5-trichlorophenyl]-acetonitrile [Formula (IV)]

2-[S-Methylthiosemicarbazide]-2-[2,3,5-trichlorophenyl]-acetamide (2 g, 5.89 mmol) was added portionwise to a solution of diphosphoryl chloride (2.97 g, 1.63 ml, 11.8 mmol) in 1,4-dioxane (16 ml) and stirred under nitrogen for six hours. The dark solution was evaporated in vacuo to leave a dark-yellow oil. The oil was dissolved in ethyl acetate (50 ml), washed with water (50 ml), saturated aqueous sodium hydrogen carbonate (50 ml), brine (50 ml), then dried over magnesium sulphate, filtered and evaporated in vacuo to give a dark-yellow oil The crude product was purified by column chromatography using 3:1 hexane:ethyl acetate as the eluent. The product, 2-[S-Methylthiosemicarbazono]-2-[2,3,5-trichlorophenyl]-acetonitrile was obtained as a yellow oil which crystallised to a yellow solid upon standing. Yield 1.16 g (61.2%). N.M.R. (d$_6$-DMSO) δ ppm: 2.20(s,1H), 3.38(broad s,3H), 7.68(broad s,1H), 7.95(d,1H), 8.12(broad s, 1H). LC/MS, Electrospray positive (M+1)$^+$=321/323.

EXAMPLE

5-Amino-6-[2,3,5-trichlorophenyl]1,2,4-triazine

Process A

Raney nickel (3.50 g, suspension in water, Fluka) was suspended in a solution of 3-thiomethyl-5-amino-6-(2,3,5trichlorophenyl)-1,2,4-triazine (1.75 g, 5.44×10$^{-3}$ mole) in absolute ethanol (30 ml) and stirred at 70° C. Hydrazine monohydrate (3.50 ml, 3.54 g, 0.11 mole) was added dropwise to the suspension over 30 min. The resulting mixture was stirred at 70–75° C. for 2 hours filtered, washed with hot absolute ethanol (3×20 ml) and the filtrate evaporated in vacuo. The residue was purified by 'flash chromatography' using 15:25 cyclohexane:ether to ether as the eluent and then by Preparative Hplc using Supelcosil ABZ column and 50% acetonitrile/water and 0.1% formic acid as the eluent. Yield 0.134 g (9%) M.p. 220–222° C., R$_t$=13.691 min, N.m.r.(d$_6$-DMSO) δ ppm: 6.90 (Broad, s,1H), 7.60 (d,1H), 7.70 (Broad, s,1H), 8.0 (d, 1H), 8.70 (s, 1H). LC/MS (EI) M$^+$=275/277.

Process B

3-Methylsulfoxy-5-amino-6-[2,3,5-trichlorophenyl]-1,2,4triazine (5.82 g, 17.2 mmol, 1 eq) was dissolved in a 1:1 mixture of THF:t-butanol (1800 ml). Sodium borohydride (915 g, 24.08 mmol, ~1.4 eq) was added in one portion and the resulting mixture was stirred at room temperature, under nitrogen, for 2 hours. All solvent was removed in vacuo to give a yellow solid which was then azeotroped with tetrahydrofuran (200 ml). 10% Aqueous citric acid (500 ml) was added slowly keeping the temperature below 20° C., followed by ethyl acetate (500 ml). The layers were sepa rated and the aqueous layer was further extracted with ethyl acetate (500 ml). Th combined organic layers were washed with saturated brine, dried over anhydrous magnesium sulfate, filtered and any volatiles were removed in vacuo to give a yellow solid.

The product was purified using column chromatography, using 20% ethyl acetate in hexane as the eluent, increasing to 60% ethyl acetate in hexane. Product-containing fractions were combined and evaporated in vacuo, affording a yellow solid, 5-amino-6-[2,3,5-trichlorophenyl]-1,2,4-triazine. Yield 1.5 g (31.7%).

N.m.r.(d$_6$DMSO) δ ppm: 7.67(d,1H), 8.02(d,1H), 8.75(s, 1H),7.0–7.2(broad s, 1H),7.7–8.0(broad s,1H). LC/MS Electrospray positive (M+1)$^+$=275/277

PHARMACY EXAMPLES

Sterile Formulations

Example A

|  | mg/ml |
| --- | --- |
| Compounds of the Invention | 0.1 mg |
| Sodium Chloride USP | 9.0 mg |
| Water for Injection USP qs to | 1 ml |

The components are dissolved in a portion of the water for injections and the solution made up to a final volume to provide 0.1 mg/ml of the compounds of the Invention. Where a salt of the compounds is used, the quantity of compounds is increased to provide 0.1 mg/ml of the free base. The solution may be packaged for injection, for example by filling and sealing into ampoules, vials or syringes. These may be aseptically filled and/or terminally sterilised by, for example, autoclaving at 121° C.

Further sterile formulations may be prepared in a similar manner to obtain alternative concentrations of the compounds.

Example B

|  | mg/ml |
| --- | --- |
| Compounds of the Invention | 0.5 mg |
| Mannitol | 50.0 mg |
| Water for Injections qs to | 1.0 ml |

Dissolve the components in a portion of the Water for Injections. Make up to final volume and mix until homogeneous. Filter formulation through a sterilising filter and fill into glass vials. Lyophilise and seal vials. Reconstitute with appropriate solvent prior to use.

Formulations for Oral Administration

Tablets may be prepared by the normal methods such as direct compression or wet granulation. The tablets may be film coated with suitable film forming materials, such as an Opadry, using standard techniques. Alternatively the tablets may be sugar coated.

Example C

Direct Compression Tablet

|  | mg/Tablet |
| --- | --- |
| Compounds of the Invention | 5.0 mg |
| Magnesium Stearate | 4.0 mg |
| Microcrystalline Cellulose( Avicel PH102) qs to | 400.0 mg |

The compounds of the Invention are passed through a 30 mesh sieve and blended with the Avicel and Magnesium Stearate. The resultant blend is compressed into tablets using a suitable tablet press fitted with 11.0 mm diameter punches so as to provide 5 mg of the Compounds of the Invention per tablet. Tablets of other strengths, containing for example 25 or 100 mg/tablet of the Compounds of the Invention may be prepared in a similar manner.

Example D

Wet Granulation Tablet

|  | mg/Tablet |
| --- | --- |
| Compounds of the Invention | 5.0 mg |
| Pregelled Starch | 28.0 mg |
| Sodium Starch Glycollate | 16.0 mg |
| Magnesium Stearate | 4.0 mg |
| Lactose qs | 400.0 mg |

The Compounds of the Invention, Lactose, Pregelled Starch and Sodium Starch Glycollate were dry mixed and then granulated using a suitable volume of Purified Water. The resultant granules were dried and then blended with the Magnesium Stearate. The dried granules were compressed using a suitable tablet press fitted with 11.0 mm diameter punches so as to provide 5 mg of the Compounds of the Invention per tablet.

Tablets of other strengths such as 25 and 100 mg/tablet were prepared.

Example E

Hard Gelatin Capsule

|  | mg/capsule |
| --- | --- |
| Compounds of the Invention | 5.0 mg |
| Microcrystalline Cellulose (Avicel PH102) qs | 700.0 mg |

The Compounds of the Invention are passed through a 30 mesh sieve and then blended with the Microcrystalline Cellulose to provide an homogeneous blend The blend may then be filled into size 0EL hard gelatin capsule shells so as to provide capsules containing 5.0 mg/capsule of Compounds of the Invention. Alternative strengths such as 25 or 100 mg/capsule of Compounds of the Invention may be made in a similar manner.

Example F

Soft Gelatin Capsule

|  | mg/capsule |
| --- | --- |
| Compounds of the Invention | 10.0 mg |
| Polyethylene Glycol | 90.0 mg |
| Propylene Glycol qs | 200.0 mg |

Blend together the Polyethylene Glycol and Propylene Glycol using heat as necessary. Stir until homogeneous. Add the Compounds of the Invention and mix until homogeneous. Fill into an appropriate gelatin mass to give soft gelatin capsules containing 200 mg of the formulation, to provide 10.0 mg/capsule of the Compounds of the Invention.

Alternative strengths for example, 5 and 25 mg/capsule of the Compounds of the Invention may be prepared in a similar manner.

Example G

| Syrup | |
|---|---|
| Compounds of the Invention | 5.0 mg |
| Sorbitol Solution | 1500.0 mg |
| Glycerol | 1000.0 mg |
| Sodium Benzoate | 5.0 mg |
| Flavour | 12.5 mg |
| Purified Water qs to | 5.0 ml |

The Sodium Benzoate is dissolved in a portion of the purified water and the Sorbitol Solution added. The Compounds of the Invention, Flavour and Glycerol are added and mixed until homogeneous. The resultant mixture is made up to volume with the purified water.

Other Formulations

Example H

| Suppository | |
|---|---|
| | mg/suppository |
| Compounds of the Invention | 10.0 mg |
| Witepsol W32, hard fat qs | 2000.0 mg |

Melt the Witepsol W32 at approximately 36° C. To a portion of this add the Compounds of the Invention and blend. Incorporate the remaining melted Witepsol W32 and blend until homogeneous. Fill mould with 2000 mg of the formulation to provide 10.0 mg/suppository of the Compounds of the Invention.

Example I

| Transdermal | |
|---|---|
| Compounds of the Invention | 5.0 mg |
| Silicone Fluid | 90.9 mg |
| Colloidal Silicone Dioxide | 5.0 mg |

Mix the silicone fluid and active together and add the colloidal silicone dioxide. The material is then dosed into a subsequently heat sealed polymeric laminate comprised of the following: polyester release liner, skin contact adhesive composed of silicone or acrylic polymers, a a control membrane which is a polyolefin (for example polyethylene or polyvinyl acetate) or polyurethane, and an impermeable backing membrane of a polyester multilaminate.

Biological Data

Activity Against voltage-gated Sodium Channels

Whole-cell voltage-clamp techniques were employed to evaluate the activity of a compound of formula (I) on the recombinant human brain type IIA Na$^+$ channel expressed in Chinese hamster ovary cells A compound of formula (I) inhibits these channels in a voltage- and use-dependent manner with an estimated $K_i$ value of 11 $\mu$M for the steady-state inactivation state, approximately 70-fold greater than the potency at the resting state ($IC_{50}$=785 $\mu$M).

The increased state selectivity and greater use-dependent inhibition compared to lamotrigine (approximately 30-fold) provides a mechanism through which a compound of formula (I) selectively blocks transmission during high frequency firing of action potentials (e.g. seizure activity). This supports the finding that a compound of formula (I) is a more potent anti-convulsant than lamotrigine and with a greater therapeutic index.

Anticonvulsant Activity

A compound of formula (I) has been shown to have anti-epileptic activity in two rodent models of generalised epilepsy, the rat maximal electroshock test (MES) which is an animal model that reflects human generalised tonic-clonic seizures and the mouse pentylenetetrazol infusion test predictive of human absence seizures and myoclonic petit mal epilepsy.

For example, male Han Wistar rats (150–200 grms) were dosed orally with a suspension of the test compound in 0.25% methylcellulose 2 hr prior to test. A visual observation is carried out just prior to testing for the presence of ataxia. Using auricular electrodes a current of 200 mA, duration 200 millisec, is applied and the presence or absence of hind limb extension noted. A compound of formula (I) exhibited an $ED_{50}$ of 1.7 mg/kg compared to 6.1 mg/kg for lamotrigine with a therapeutic index (ratio of the ataxia $ED_{50}$ and MES $ED_{50}$) of 23.7 compared to 3.3 for lamotrigine.

A compound of formula (I) exhibited an $ED_{50}$ of 3.8 mg/kg in the mouse pentylenetetrazol infusion test (time to second twitch) when dosed 1 hr post PTZ, compared to an $ED_{50}$ of 8.4 mg/kg for lamotrigine.

Analgesic Activity

A compound of formula (I) has also been shown to have analgesic activity in models of pain. Three hours after intraplantar carrageenan administration (100 $\mu$l of 2%) in the rat there is a reduction in weight bearing on the inflamed paw and an increase in paw volume consistent with acute hyperalgesia and inflammation. A compound of formula (I), administered orally 30 minutes prior to carrageenan, produced a doserelated inhibition of the carrageenan-induced reduction in weight bearing with an $ED_{50}$ of 7.5 mg/kg compared to 23.5 mg/kg for lamotrigine. A compound of formula (I) also showed significant anti-inflammatory activity in this model at 30 mg/kg (50% reduction in paw volume).

Activity Against MPTP Induced Neurotoxicity

The mouse MPTP model is generally used as a model of Parkinson's disease.

Male C57BL/6 mice received four intraperitoneal injections of MPTP.HCl (15 mg of free base per kg; Research Biochemicals) in saline at 2 hour intervals. Control mice received saline only. The test-compound was administered as four subcutaneous injections in olive oil at 2 hour intervals, 30 minutes before each MPTP injection.

Seven days after MPTP injection the mice were sacrificed and the striata dissected out, immediately frozen, and stored at −80° C. until analysis. On the day of assay issue samples were sonicated in 10 volume (wt./vol.) of 0.1 M perchloric acid containing 1.9 mM sodium hydrosulfite and 1.6 mg/ml DBA-HBr. After centrifugation (2800 g, 10 min at room temperature) and filtration (pore size 0.5 $\mu$m, Millipore), the supernatant was transferred to a vial and placed in the automatic sampler (M231XL, Gilson). Dopamine content was measured by high performance liquid chromatography.

A compound of formula (I) produced 75% protection against dopamine depletion when dosed at 3 mg/kg (×4) and 98% protection when dosed at 10 mg/kg (×4).

What is claimed is:

1. A method of treating a patient suffering from, or susceptible to epilepsy by administration of an effective amount of a compound of formula (I)

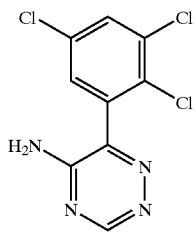

(I)

and salts thereof.

2. A method of treating a patient suffering from, or susceptible to bipolar disorder by administration of an effective amount of a compound of formula (I)

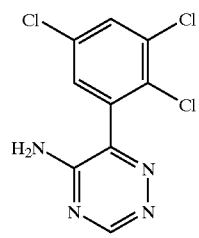

(I)

and salts thereof.

3. A method of treating a patient suffering from, or susceptible to pain by administration of an effective amount of a compound of formula (I)

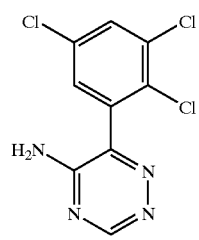

(I)

and salts thereof.

* * * * *